United States Patent [19]

Laguzza

[11] Patent Number: 4,622,398
[45] Date of Patent: Nov. 11, 1986

[54] DIALKYLAMINOTETRAHYDROQUINAZOLINE

[75] Inventor: Bennett C. Laguzza, Indianapolis, Ind.

[73] Assignee: Eli Lilly and Company, Indianapolis, Ind.

[21] Appl. No.: 748,116

[22] Filed: Jun. 24, 1985

[51] Int. Cl.$^4$ .......................................... C07D 239/84
[52] U.S. Cl. .................................. 544/292; 544/283; 544/286
[58] Field of Search ..................... 544/292, 283, 286

[56] References Cited

U.S. PATENT DOCUMENTS

| | | | |
|---|---|---|---|
| 3,496,179 | 2/1970 | Hess | 544/292 |
| 4,198,415 | 4/1980 | Kornfeld et al. | 546/164 |
| 4,235,776 | 11/1980 | Kornfeld et al. | 260/326.1 |
| 4,235,909 | 11/1980 | Bach et al. | 546/84 |
| 4,276,300 | 6/1981 | Bach et al. | 548/369 |
| 4,501,890 | 2/1985 | Nichols et al. | 514/267 |

*Primary Examiner*—Glennon H. Hollrah
*Assistant Examiner*—James H. Turnipseed
*Attorney, Agent, or Firm*—Charles W. Ashbrook; James L. Rowe

[57] ABSTRACT

2-Permissibly-substituted-6-dialkylaminotetrahydroquinazolines, receptor agonists.

9 Claims, No Drawings

DIALKYLAMINOTETRAHYDROQUINAZOLINE

BACKGROUND OF THE INVENTION

Certain complex amides of lysergic acid (I, R=OH, also named as 9-ergolene-8β-carboxylic acid) are found in ergoted rye; i.e., rye contaminated by the growth of the filamentous fungus *Claviceps purpurea*. Persons eating bread prepared from ergoted rye were subject to ergot poisoning, known in the Middle Ages as St. Anthony's Fire because of the feeling of intense heat in the extremities. Ergot poisoning was often fatal. The peripheral vasoconstrictor properties of the ergot alkaloids, as a group, is responsible for the fatalities seen with ergot poisoning, with gangrene of the extremeties being a common precipitating factor.

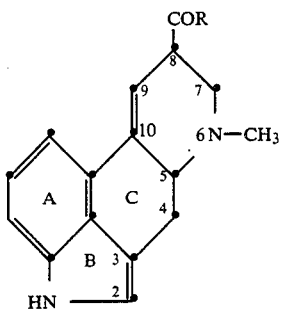

Two dozen ergot alkaloids have been characterized from isolates from *Claviceps purpurea* infestations. Derivatives of lysergic acid include the simple amides, ergine (R=NH₂) and ergonovine (ergometrine)

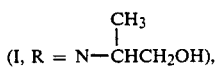

and the pepetide alkaloids (R=a complex amide derived from a cyclized polypeptide) including ergotamine, ergosine, ergocornine, ergocryptine, ergocristine, etc. The corresponding alkaloids based on isolygergic acid (9-ergolene-8α-carboxylic acid) are also present and are named by changing the "ine" ending to "inine"; e.g. ergotaminine, ergosinine, etc.

The ergot alkaloids as a group have several interesting pharmacologic activities; uterine contraction (oxytocic action), peripheral vasoconstriction, adrenergic blockade, and serotonin antagonism as well as varied CNS activities including the production of hallucinations. Certain of the alkaloids individually are used to produce post-partum uterine contractions and in the treatment of migraine. Pharmacologic activity, toxicity and central effects vary from alkaloid to alkaloid. In general, hydrogenation of the delta-9 double bond results in compounds of lowered activity as regards peripheral action but adrenolytic and central inhibition of vasomotor centers is enhanced.

Derivatives of lysergic acid and dihydrolysergic acid are too numerous to mention, but include, generically, substitution on the indole nitrogen, and at C-2 (α-bromocryptine is a 2-bromo derivative), replacement of the carboxamide function at C-8 by various groups, particularly cyanomethyl, methylthiomethyl, methoxymethyl as well as substitution of simpler amide groups (butanolamide=methysergide) for the complex "poly-peptide chains" or simple hydroxy amides of the natural alkaloids.

There has been considerable speculation, frequently followed by a synthetic effort, as to what portions of the ergoline molecule are responsible for activity; i.e., are part-structures possible which retain, perhaps selectively, the pharmacologic activity of the parent alkaloid? One part-structure which has been examined is the aminotetrahydronaphthalene structure II from which the B and D rings of an ergoline have been subtracted.

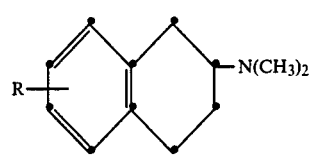

where R is carboxamide, hydroxy, amino etc. The elements of a β-phenethylamine can also be discerned from I using the phenyl ring and carbons 5 and 10 plus the nitrogen at 6, a part structures in which only the A ring is retained. In addition, tricyclics lacking the B (indole) ring as well as benz[c]indoles (lacking the D ring—see U.S. Pat. No. 4,110,339) have been prepared. None of these part-structures seemed to have the desired degree of activity as regards the dopamine D-2 agonist activity (prolactin inhibition etc) of ergocornine, dihydroergocornine, lergotrile or pergolide (U.S. Pat. Nos. 3,920,664, 4,054,660 and 4,166,182, for example). However, recently Kornfeld and Bach have found that the A ring of an ergoline is not required for D-2 agonist activity. These new part structures are named as hexahydropyrrolo[4,3-g]quinolines—see U.S. Pat. No. 4,235,909. A related structure, a hexahydropyrazolo[4,3-g]quinoline, U.S. Pat. No. 4,198,415, also had excellent D-2 agonist action. The corresponding 2-ring compounds, in which the D ring of the ergoline is opened to leave a dialkylamine substituent on the C ring, are also active D-2 agonists—see U.S. Pat. Nos. 4,235,226 for the amino-substituted isoindoles, and 4,276,300 for the amino-substituted indazoles (analogous to the three-ring pyrazoles). It has now been found that other hetero ring systems than pyrrole and pyrazole can be attached to the perhydroquinoline ring (rings B+C of an ergoline). One of these is a pyrimidine—see Nichols and Kornfeld, U.S. Pat. No. 4,501,890.

2-Amino-6-dialkylaminotetrahydroquinazolines, (a two-ring benzopyrimidine) are not known.

SUMMARY OF THE INVENTION

This invention provides tetrahydroquinazolines XX of the formula

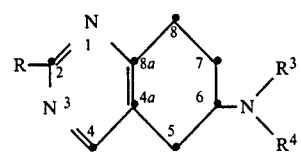

wherein R is H, S—C₁₋₃alkyl, OH, O—CO—C₁₋₂alkyl (lower acyloxy), or NR¹R², R¹ and R² are independently H, methyl, ethyl or n-propyl, and R³ and R⁴ are independently methyl, ethyl, n-propyl or allyl; and pharmaceutically-acceptable acid addition salts thereof formed with non-toxic acids.

A preferred group of compounds according to XX are those in which $R^3$ and $R^4$ are both methyl, or are both n-propyl or allyl. Another preferred group are those compounds according to XX in which R is $NR^1R^2$. A still further preferred group of compounds are those in which R is $NR^1R^2$ and $R^1$ and $R^2$ are both H.

The compounds of this invention wherein R is H, $NR^1R^2$ or OH have receptor agonist activity; i.e., they can increase the effective concentration of a neurohormone. For example, compounds according to XX in which both $R^3$ and $R^4$ are allyl or n-propyl, are dopamine agonists, particularly dopamine D-2 agonists, capable of increasing the effective concentration of dopamine in the brain.

Compounds according to XX in which R is $C_{1-3}$ alkyl-S are primarily intermediates in that they can be transformed to receptor agonists by synthetic procedures available in the art.

Also included within the scope of this invention are acid addition salts of the bases represented by XX. The above compounds contain at least two basic nitrogens, one the amine group at C-6 and the other a ring nitrogen in the fused heterocyclic ring (N-1 or N-3). In compounds according to XX wherein R is $NR^1R^2$ and neither $R^1$ nor $R^2$ is lower acyloxy, there is a third basic nitrogen, the $NR^1R^2$ group. The nitrogen of the C-6 amino group is generally the most basic of the amine function and readily forms acid addition salts. Strong inorganic acids such as the mineral acids, or strong organic acids such as p-toluenesulfonic acid, can form di salts with one of the other amine functions in the compounds of this invention when employed in excess.

Pharmaceutically-acceptable acid addition salts of the compounds of this invention thus include mono or di salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxyalkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, α-hydroxybutyrate, glycolate, malate, tartrate, methanesulfonate, propanesulfonate, naphthalene-1-sulfonate, naphthalene-2-sulfonate and the like salts.

The compounds of this invention according to XX above where R is $NR^1R^2$. can be prepared according to the following reaction scheme:

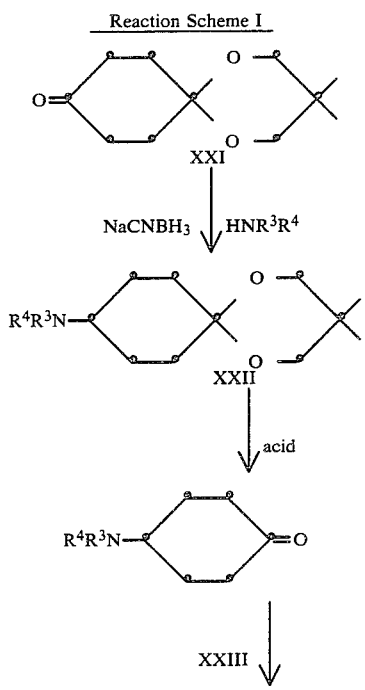

-continued
Reaction Scheme I

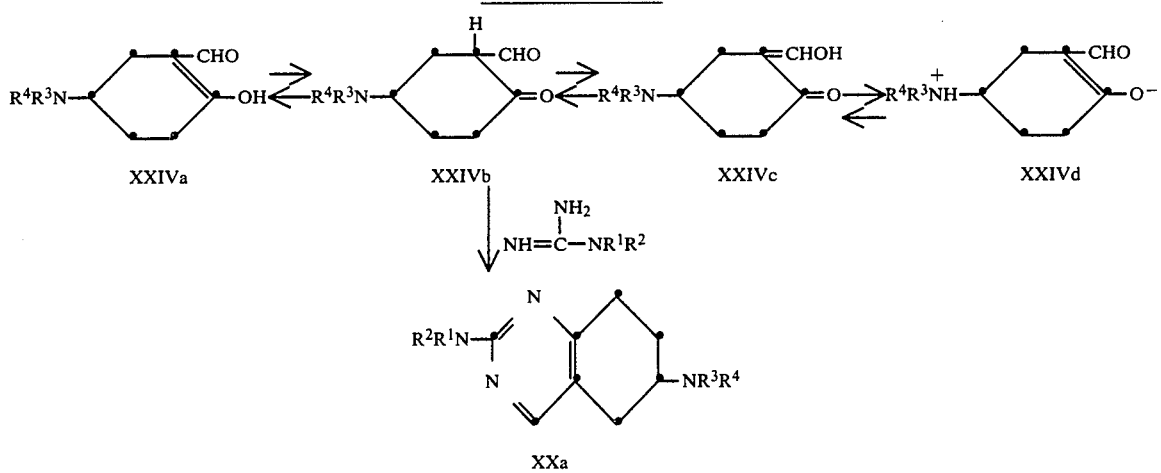

wherein $R^1$, and $R^2$, $R^3$ and $R^4$ have their previous meanings.

In Reaction Scheme I above, a blocked, as by ketal formation, cyclohexan-1,4-dione, is reductively aminated with a secondary amine, $HNR^3R^4$, using a borohydride in a mutual inert solvent. As a starting material, the ketal of cyclohexane-1,4-dione with 2,2-dimethyl-1,3-propanediol (XXI) is commercially available and is therefore preferred although monoketals with other diols; i.e., ethylenediol, 1,3-propylenediol and the like, may also be used. Sodium cyanoborohydride is the reducing agent of choice, although other metal hydrides can be employed. Ethers, and particularly cyclic ethers such as THF, are the solvents of choice.

The product of the reductive amination, XXII, is next deprotected by treatment with acid to yield a 4-di(alkyl or allyl)aminocyclohexanone. Formylation alpha to the carbonyl with ethylformate and a base, conveniently t-BOK (potassium tertiary butoxide), yields the tautomeric mixture represented by XXIV a-d. Alternatively dimethylformamide dimethylacetal or tris(dimethylamino) methane can be used to yield 4-di(alkyl or allyl)amino-2-dimethylaminomethylenecyclohexanone XXV

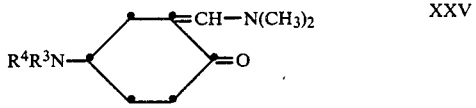

(The same compound can be prepared by reacting XXIV a-d with dimethylamine). XXV has a "masked" formyl group but reacts with guanidine or a substituted guanidine to form the quinazoline XXa (XX where R is $NR^1R^2$).

Reaction of XXIVa-d or XXV with formamidine or an S-alkylthiourea yield XXb (XX where R is H) and XXc (XX where R is $C_{1-3}$ alkyl-S) respectively

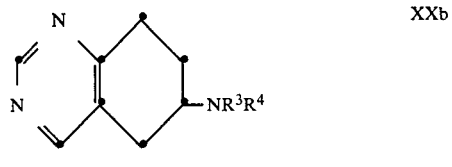

Compounds according to XX wherein R is OH—XXd (XX where R is OH) are prepared from the corresponding S—$C_{1-3}$alkyl derivative by acidic hydrolysis, conveniently with concentrated hydrochloric acid.

Compounds according to XX above wherein R is $C_{1-3}$-alkyl-CO-O are prepared by acylating the corresponding hydroxy compound (R=OH).

Compounds according to XX above have an asymmetric carbon, the C-6 carbon to which the amino group ($NR^3R^4$) is attached. Thus, compounds represented by XX above include two optical isomers occurring as a (±) or dl pair or racemate. Resolution of a (±) pair of this invention into its optical antipodes can be accomplished by the usual cut-and-try procedures used by those skilled in the art. The separated optical isomers are included within the scope of my invention.

Compounds preparable by the above procedures which illustrate the scope of my invention include:

(−)-2,6-bis(dimethylamino)-5,6,7,8-tetrahydroquinazoline methanesulfonate, (+)-2,6-bis(methyl-n-propylamino)-5,6,7,8-tetrahydroquinazoline hydrobromide, (±)-2-dimethylamino-6-ethyl-n-propylamino-5,6,7,8-tetrahydroquinazoline sulfate, (±)-2-diethylamino-6-di-n-propylamino-5,6,7,8-tetrahydroquinazoline hydrobromide, (±)-6-diallylamino-5,6,7,8-tetrahydroquinazoline maleate, (−)-2-hydroxy-6-methyl-allylamino-5,6,7,8-tetrahydroquinazoline succinate, (±)-2-propionoxy-6-allyl-n-propylamino-5,6,7,8-tetrahydroquinazoline tartrate, (−)-2-amino-6-diallylamino-5,6,7,8-tetrahydroquinazoline dinitrobenzoate, (±)-2-ethylthio-6-dimethylamino-5,6,7,8-tetrahydroquinazoline phosphate and the like.

This invention is further illustrated by the following specific examples.

EXAMPLE 1

Preparation of (±)-2-Amino-6-di-n-propylamino-5,6,7,8-tetrahydroquinazoline

About 125 ml of methanol were added to a 500 ml round bottom flask under a nitrogen blanket. Forty-two ml of di-n-propylamine were added and the resulting solution cooled to about 0° in an ice/water bath. Twenty ml of 5N methanolic hydrochloric acid were added. The reaction mixture was stirred until salt formation was complete. Ten grams of 1,4-cyclohexanedione-mono-2,2-dimethyltrimethylene ketal were added as a solid. The reaction mixture was stirred with cooling for several minutes at which point 2.25 g of sodium cyanoborohydride were added in one portion. A white slurry developed rapidly which was stirred in the cold for several minutes and then at room temperature under a nitrogen blanket for about 30 hours. An additional 2.2 g of sodium cyanoborohydride were added. After an additional 24 hours stirring at room temperature, at which time TLC (chloroform/methanol 95:5) indicated a new spot and the absence of the spot corresponding to starting material. The reaction mixture was filtered and the filter cake washed with methanol. The filtrate and wash were combined and the solvent evaporated therefrom to yield a thick, white slurry. The slurry was cooled to about 0° C. and 100 ml of 1N hydrochloric acid were added with stirring. The resulting solution was extracted twice with equal volumes of ether. The ether extracts were separated and discarded. The aqueous layer was cooled and then made basic by the addition of 5N aqueous sodium hydroxide (pH=12). The basic layer was extracted three times with 50 ml portions of methylene dichloride. The methylene dichloride extracts were combined, the combined extracts were washed once with saturated aqueous sodium bicarbonate and were then dried. Evaporation of the solvent in vacuo yielded a yellow oil containing some solid; weight=6.26 g. The residue was flash chromatographed over 100:1 ether/triethylamine solvent as eluant. Fifty ml fraction were taken. Fractions 10–15 were shown by TLC to contain the desired material. These fractions were combined and concentrated in vacuo to yield 5.40 g of a nearly colorless oil comprising 4-di-n-propylamino-1-cyclohexanone 2,2-dimethyltrimethylene ketal.

The ketal group was removed by dissolving 4.4 g of the above ketal in 110 ml of 6N hydrochloric acid with stirring under a nitrogen atmosphere for 48 hours at room temperature. The colorless solution was extracted with 50 ml of ether; the ether extract was discarded. The acidic solution was then made basic by the addition of an excess of 5N aqueous sodium hydroxide. The resulting cloudy mixture was extracted three times with 50 ml portions of methylene dichloride. The methylene dichloride extracts were combined, and the combined extracts washed three times with 50–75 ml portions of saturated aqueous sodium bicarbonate. The organic layer was then dried, and the solvent removed in vacuo to yield 2.96 g of a pale yellow oil comprising 4-di-n-propylaminocyclohexanone formed in the above reaction. The compound showed the expected carbonyl peak at 5.85μ in the infrared. The infrared also showed no hydroxyl absorption.

Two grams of 4-di-n-propylcyclohexanone were placed in a dry flask under a nitrogen atmosphere. Eight ml of anhydrous ethanol were added. Next, 2.1 ml of tris (dimethylamino)methane were added (under the surface of the solution) by syringe. The resulting mixture was heated at about 100° C. under a nitrogen atmosphere. After about 5 hours, the resulting dark brown solution was cooled and allowed to stand under nitrogen over night. The reaction mixture was next concentrated, a solution of 1.10 g of guanidine carbonate in 5 ml of anhydrous ethanol was added. The reaction mixture was heated at reflux temperature with stirring for about 2 hours. An additional 3 ml of anhydrous ethanol were added. The reaction mixture was heated and stirred overnight and then was cooled to room temperature. A yellow solid precipitated upon cooling, which solid was collected by filtration. The solid thus obtained was washed several times with ether; yield=726 mg.

The filtrate was diluted with 150 ml of ether and a pale yellow solid again precipitated which solid was collected by filtration and the filter cake washed with ether. The combined yellow solids were dissolved in ethanol. The hot ethanol solution was filtered through Celite and then cooled. Several crops of crystalline material comprising (±)-2-amino-6-di-n-propylamino-5,6,7,8-tetrahydroquinazoline were obtained; weight=240 mg. The hydrochloride salt was prepared by dissolving the above free base in anhydrous methanol and saturating the methanol solution at ice bath temperatures with gaseous HCl. The methanol solution was filtered and then concentrated to yield 264 mg of (±)-2-amino-6-di-n-propylamino-5,6,7,8-tetrahydroquinazoline dihydrochloride. The compound was recrystallized by dissolution in a minimum amount of DMF (about 3 ml) and then adding ether in dropwise fashion until a yellow solid precipitated. The solid was filtered, and the filter cake washed with ether. A final yield of 245 mg of the dihydrochloride salt were obtained.

Analysis calculated: C, 52.34; H, 8.16; N, 17.44; Found: C, 52.23; H, 8.44; N, 17.20.

(After blocking at 120° C.)

Mass spectrum: molecular ion at 248, other peaks at 219 and 148.

Following the above procedure (±)-2-methylamino-6-di-n-propylamino-5,6,7,8-tetrahydroquinazoline was prepared from di-n-propyaminocyclohexanone by reaction with tris-(dimethylamino methane and N-methylguanidine hydrochloride tris-(dimethylamino)methane. Five hundred mg of starting 4-di-n-propylaminocyclohexanone gave 306 mg of a brown oil comprising the free base which was converted to the dihydrochloride salt and purified by dissolution in DMF and the DMF solution added to ether. Crystalline (±)-2-methylamino-6-di-n-propylamino-5,6,7,8-tetrahydroquinazoline dihydrochloride thus prepared was obtained as a methanol solvate after recrystallization from methanol.

Analysis calculated: C, 52.31; H, 8.78; N, 15.25; Found: C, 52.34; H, 8.50; N, 15.30.

Mass spectrum: molecular ion at 262, another peak at 162.

Following the above procedure, 1.01 g of 4-di-n-propylaminocyclohexanone were reacted with ethylformate in the presence of potassium t-butoxide. The intermediate 2-formyl product was reacted without further purification with N-dimethylguanidine to yield (±)-2-dimethylamino-6-di-n-propylaminoquinazoline as the free base in impure form. The crude free base was flash chromatographed over silica using a 100:1:1 ether/methanol/triethylamine solvent as the eluant. NOTE: The term "flash chromatography" as used refers to the procedure of Still et al., *J. Org. Chem.*, 43 2923 (1978). Fractions containing the desired product as shown by TLC were combined to yield a brown oil weighing about 727 mg. 365 mg of this product were further purified by chromatography over Merck silica production plates using 100:2:1 ether/methanol/triethylamine as the eluant; 283 mg of a yellow oil comprising purified (±)-2-dimethylamino-6-di-n-propylamino-5,6,7,8-tetrahydroquinazoline were obtained. The free base was converted to the dihydrochloride salt in ethereal solution, using the procedure of the above example. 222 mg of white powder comprising the dihydrochloride salt was obtained. Mass spectrum analysis of the salt showed a molecular ion at 276.

EXAMPLE 2

Preparation of (±)-6-Di-n-propylamino-5,6,7,8-tetrahydroquinazoline

A solution prepared from 1.16 g of potassium t-butoxide in 50 ml of THF was placed in a dried round-bottom flask under a nitrogen atmosphere. The solution was cooled to about −74° C. A second solution containing 1.64 ml of ethyl formate and 1.0 g of 4-di-n-propyl aminocyclohexanone in 20 ml of THF was added in dropwise fashion thereto, while maintaining the temperature at about −74° C. Residual reagents were added with an additional 5 ml of THF. The resulting pale yellow solution was stirred while being allowed to slowly warm to about 0° C. 0.86 ml of glacial acetic acid were then added. The resulting yellow slurry was evaporated to dryness in vacuo leaving as a residue an amorphous orange-yellow solid comprising 4-di-n-propylamino-2-formylcyclohexanone formed in the above reaction. A solution of 629 mg of formamidine acetate in 20 ml of anhydrous ethanol was added with stirring. The resulting reaction mixture was heated to refluxing temperature under nitrogen. After about 2 hours, TLC indicated that the reaction had gone substantially to completion, but refluxing was continued for another 2.5 hours. The reaction mixture was then cooled in an ice bath and about 200 ml of 0.1N aqueous sodium hydroxide added. The alkaline mixture was extracted with four 50 ml portions of methylene dichloride. The methylene dichloride extracts were combined, the combined extracts dried and the solvent evaporated therefrom in vacuo to yield 1.0 g of a yellow solid comprising (±)-6-di-n-propylamino-5,6,7,8-tetrahydroquinazoline formed in the above reaction. The solid was dissolved in a 4:6 ether/hexane solvent mixture and the solution filtered to yield, after evaporation of the solvent 507 mg of a bright yellow solid. The solid was flash chromatographed over silica using 100:2:1 ether/methanol/triethylamine as the eluant. Fractions containing the desired tetrahydroquinazoline, as determined by TLC, were combined and the solvent evaporated therefrom to yield 160 mg. Distillation of the free base at 0.025 torr. gave about 120 mg of purified (±)-6-di-n-propylamino-5,6,7,8-tetrahydroquinazoline. This compound save a single spot by TLC using the same eluant system. Molecular ion by mass spectrum at 232.

EXAMPLE 3

Preparation of (±)-2-Methylthio-6-di-n-propylamino-5,6,7,8-tetrahydroquinazoline Following the procedure of Example 2, 1 g of 4-di-n-propylaminocyclohexanone was converted to the corresponding 2-formyl derivative with ethylformate in the presence of potassium t-butoxide (t-BOK) in THF solution. The reaction mixture was quenched with acetic acid as in Example 1 and the orange-yellow solid was obtained by evaporation to dryness. A solution of 835 mg of S-methylthiourea sulfate in 20 ml of absolute ethanol was added to the residue and the reaction mixture was heated to reflux temperature for 4.5 hours. The reaction mixture was then cooled, and the cooled solution, previously made basic (pH=8.5–9) by the addition of dilute aqueous sodium hydroxide, was added to 200 ml of saturated aqueous sodium bicarbonate. The alkaline layer was extracted with three 50 ml portions of methylene dichloride. The methylene dichloride extracts were combined, the combined extracts dried, and the volatile constituents evaporated therefrom to give about 1.5 g of a brown oil comprising (±)-2-methylthio-6-di-n-propylamino-5,6,7,8-tetrahydroquinazoline formed in the above reaction. Flash chromatography of the product over silica using a 60:40:2:1 hexane/ether/methanol/triethylamine solvent mixture as the eluant gave several fractions shown by TLC to contain the desired material. These fractions were combined, and the solvent evaporated therefrom in vacuo. Distillation of the residue at 0.05 torr. yielded 350 mg of (±)-2-thiomethyl-6-di-n-propylamino-5,6,7,8-tetrahydroquinazoline distilling in the range of 170°–180° C.

Analysis calculated: C, 64.47; H, 9.02; N, 15.04; Found: C, 64.24; H, 9.26; N, 14.78.

Molecular ions by mass spectrum equaled 279.

EXAMPLE 4

Preparation of (±)-2-Hydroxy-6-di-n-propylamino-5,6,7,8-tetrahydroquinazoline A solution of 121 mg of (±)-2-methylthio-6-di-n-propylamino-5,6,7,8-tetrahydroquinazoline in 2 ml of 12N hydrochloric acid was heated to reflux temperature for about 3.5 hours. The solution was then concentrated in vacuo to a brown oily residue. (±)-2-Hydroxy-6-di-n-propylamino-5,6,7,8-tetrahydroquinazoline dihydrochloride thus prepared was purified by recrystallization from a methanol/ethyl acetate solvent mixture. Eighty-five mg of the dihydrochloride salt were obtained which melted at about 218°–223° C. Molecular ion at 249 by mass spectrum analysis.

As previously stated, the compounds of this invention are receptor agonists; i.e., they are capable of increasing the quantities of various neurohormones—dopamine and norepinephrine in particular—available for interaction with specific receptors. For example, compounds according to XX wherein R is $NR^1R^2$, and $R^3$ and $R^4$ are both n-propyl, are specific dopamine D-2 agonists. One of such dopamine agonist activities is the inhibition of prolactin secretion, as demonstrated according to the following protocol.

Adult male rats of the Sprague-Dawley strain weighing about 200 g were housed in an air-conditioned room with controlled lighting (lights on 6 a.m.–8 p.m.) and fed lab chow and water ad libitum. Each rat received an intraperitoneal injection of 2.0 mg of reserpine in aqueous suspension 18 hours before administration of the test drug. The purpose of the reserpine was to keep the rat prolactin levels uniformly elevated. The compound was dissolved in 10 percent ethanol, and injected intraperitoneally at doses of 0.017, 0.03, 0.17 and 0.3 μmoles/kg. The compound was administered at each dose level to a group of 10 rats, and a control group of 10 intact males received an equivalent amount of 10 percent ethanol. One hour after treatment, all rats were killed by decapitation, and 150 μl aliquots of serum were assayed for prolactin.

The difference between the prolactin level of the treated rats and prolactin level of the control rats, divided by the prolactin level of the control rats gives the percent inhibition of prolactin secretion attributable to the given dose. Inhibition percentages are given in Table 1 below for compounds according to XX above. In the tables, columns 1 and 2 give substitution patterns for the basic structures at the head of the Table, column 3 the form (salt or free base—FB), and column 4, the percent prolactin inhibition at the specified dose level.

TABLE 1

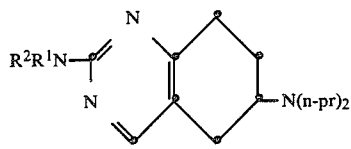

| $R^1$ | $R^2$ | Form | 50 μg/kg |
|---|---|---|---|
| H | H | 2 HCl | 34 |
| $CH_3$ | H | 2 HCl | 50 |

Dopamine agonists, according to XX have been found to affect turning behavior in 6-hydroxydopamine-lesioned rats in a test procedure designed to uncover compounds useful for the treatment of Parkinsonism. In this test, nigroneostriatal-lesioned rats are employed, as prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period.

Results obtained from such testing are set forth in Table 2 below. In the table, columns 1 and 2 give the substitution pattern for the compound at the head of the table, column 3, the salt form, and column 4, the average number of turns observed in first 15 minutes after end of latency period at a 100 mcg/kg dose.

TABLE 2

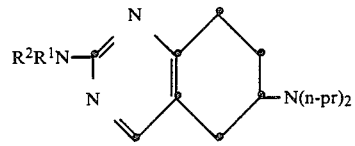

| $R^1$ | $R^2$ | Form | 100 mcg/kg |
|---|---|---|---|
| H | H | 2 HCl | 53 |
| $CH_3$ | H | 2 HCl | 50 |

TABLE 2-continued

| $R^1$ | $R^2$ | Form | 100 mcg/kg |
|---|---|---|---|
| $CH_3$ | $CH_3$ | 2 HCl | 50 |

The compounds according to XX also reduce the blood pressure of spontaneously hypertensive rats, as illustrated by the following experiment:

Adult male spontaneously hypertensive rats (SHR) (Taconic Farms, Germantown, N.Y.), weighing approximately 300 g. were anesthetized with pentobarbital sodium (60 mg./kg., i.p.). The trachea was cannulated and the SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation.

Table 3 which follows gives the results of this test. In Table 3, columns 1 and 2 give the substitution pattern for the tetrahydroquinazoline, column 3 the form and column 5 the change in mean arterial blood pressure. The drug dosage was 1000 mcg/kg.

TABLE 3

| $R^1$ | $R^2$ | Percent Changes Form | decrease in mean arterial blood pressure |
|---|---|---|---|
| H | H | 2 HCl | −49.3 |
| $CH_3$ | H | 2 HCl | −18.5 |
| $CH_3$ | $CH_3$ | 2 HCl.MeOH | −14.4 |

(±)-6-Di-n-propylamino-5,6,7,8-tetrahydroquinazoline at a 1 mg/kg dose gave a 5.2% maximal lowering of arterial blood pressure in SHR.

The compounds of this invention are administered for therapeutic purposes in a variety of formulations as illustrated below.

Hard gelatin capsules are prepared using the following ingredients:

| | Quantity (mg./capsule) |
|---|---|
| Active compound | .1–2 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
| --- | --- |
| Active compound | .1-2 mg |
| Cellulose, microcrystalline | 400 |
| Silicon dioxide, fumed | 10 |
| Stearic acid | 5 |

The components are blended and compressed to form tablets.

Alternatively, tablets each containing 0.1-2 mg. of active ingredient are made up as follows:

| Active ingredient | .1-2 mg. |
| --- | --- |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-°60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets.

Capsules each containing 0.1-2 mg. of medicament are made as follows:

| Active ingredient | .1-2 mg. |
| --- | --- |
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 0.1-2 mg. of medicament per 5 ml. dose are made as follows:

| Active ingredient | .1-2 mg. |
| --- | --- |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

For oral administration, tablets, capsules or suspensions containing from about 0.1 to about 2 mg. of active drug per dose are given 3-4 times a day, giving a daily dosage of 0.3 to 8 mgs. or, for a 75 kg person, about 4.0 to about 107 mcg/kg. The intravenous dose is in the range from about 0.1 to about 100 mcg./kg.

I claim:

1. A compound of the formula

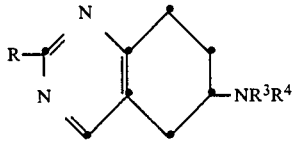

wherein R is H, OH, $C_{1\text{-}2}$alkyl-CO-O, $C_{1\text{-}3}$alkyl-S or $NR^1R^2$ wherein $R^1$ and $R^2$ are individually H, methyl ethyl and n-propyl and wherein $R^3$ and $R^4$ are individually methyl, ethyl, n-propyl or allyl; and pharmaceutically-acceptable, acid addition salts thereof.

2. A compound according to claim 1 in which R is $NR^1R^2$.

3. A compound according to claim 1 in which both $R^1$ and $R^2$ are H.

4. A compound according to claim 1 in which $R^1$ and $R^2$ are each either H or methyl.

5. A dihydrochloride salt of a compound according to claim 2.

6. A compound according to claim 1 in which both $R^3$ and $R^4$ are n-propyl.

7. A compound according to claim 1, said compound being (±)-2-amino-6-di-n-propylamino-5,6,7,8-tetrahydroquinazoline.

8. A compound according to claim 2, said compound being (±)-2-methylamino-6-di-n-propylamino-5,6,7,8-tetrahydroquinazoline.

9. A compound according to claim 2, said compound being (±)-2-dimethylamino-6-di-n-propylamino-5,6,7,8-tetrahydroquinazoline.

* * * * *